United States Patent
Tanabe et al.

(10) Patent No.: US 9,596,977 B2
(45) Date of Patent: Mar. 21, 2017

(54) IMAGING ELEMENT, IMAGING DEVICE, ENDOSCOPE, ENDOSCOPE SYSTEM, AND METHOD OF DRIVING IMAGING ELEMENT

(71) Applicant: OLYMPUS CORPORATION, Tokyo (JP)

(72) Inventors: Yuzuru Tanabe, Niiza (JP); Katsumi Hosogai, Tsukuba (JP); Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/825,723

(22) Filed: Aug. 13, 2015

(65) Prior Publication Data

US 2015/0342443 A1   Dec. 3, 2015

Related U.S. Application Data

(63) Continuation of application No. PCT/JP2014/059270, filed on Mar. 28, 2014.

(30) Foreign Application Priority Data

Apr. 18, 2013   (JP) .................................. 2013-087535

(51) Int. Cl.
*A61B 1/00*   (2006.01)
*H04N 5/06*   (2006.01)
(Continued)

(52) U.S. Cl.
CPC .......... *A61B 1/00006* (2013.01); *A61B 1/045* (2013.01); *A61B 1/05* (2013.01);
(Continued)

(58) Field of Classification Search
None
See application file for complete search history.

(56) References Cited

U.S. PATENT DOCUMENTS 7,187,020 B2 * 3/2007 Mabuchi ........... H01L 27/14632
257/113
7,671,912 B2   3/2010 Abe et al.
(Continued)

FOREIGN PATENT DOCUMENTS

JP   2001-111900 A   4/2001
JP   2004-172950 A   6/2004
(Continued)

OTHER PUBLICATIONS

International Search Report dated Jul. 8, 2014 issued in PCT/JP2014/059270.
(Continued)

*Primary Examiner* — Reza Aghevli
(74) *Attorney, Agent, or Firm* — Scully, Scott, Murphy & Presser, PC

(57) ABSTRACT

An imaging element includes: a plurality of pixels arranged into a two-dimensional matrix, configured to receive light from outside, and configured to generate and output an imaging signal according to an amount of light received; a first transfer line connected to the pixel and configured to transfer the imaging signal; a pixel selection unit configured to perform a selection operation of selecting a selection target pixel from among the plurality of pixels in order to read the imaging signal out to the first transfer line and a de-selection operation of canceling the selection of the pixel being selected; and control unit configured to control the pixel selection unit. The control unit performs the selection operation of selecting a new selection target pixel after
(Continued)

performing the de-selection operation on the basis of a synchronization signal from outside.

4 Claims, 14 Drawing Sheets

(51) Int. Cl.
    *H04N 5/341*     (2011.01)
    *H04N 5/63*     (2006.01)
    *H04N 5/376*     (2011.01)
    *H04N 5/374*     (2011.01)
    *A61B 1/05*     (2006.01)
    *G02B 23/24*     (2006.01)
    *A61B 1/045*     (2006.01)
    *H04N 5/378*     (2011.01)
    *H04N 7/18*     (2006.01)

(52) U.S. Cl.
    CPC .......... *G02B 23/2484* (2013.01); *H04N 5/06* (2013.01); *H04N 5/341* (2013.01); *H04N 5/374* (2013.01); *H04N 5/378* (2013.01); *H04N 5/3765* (2013.01); *H04N 5/63* (2013.01); *A61B 1/00009* (2013.01); *H04N 7/183* (2013.01)

(56) References Cited

U.S. PATENT DOCUMENTS

| | | | |
|---|---|---|---|
| 8,013,336 B2 | 9/2011 | Mabuchi | |
| 8,076,697 B2 | 12/2011 | Mabuchi | |
| 8,081,245 B2 | 12/2011 | Itano et al. | |
| 8,368,790 B2 | 2/2013 | Itano et al. | |
| 8,482,643 B2 | 7/2013 | Abe et al. | |
| 8,994,863 B2 | 3/2015 | Abe et al. | |
| 2007/0132868 A1* | 6/2007 | Lee | H03M 1/1019 348/308 |
| 2009/0303362 A1* | 12/2009 | Ebihara | H04N 5/353 348/296 |
| 2010/0225579 A1* | 9/2010 | Kwak | H04N 5/353 345/156 |
| 2011/0205417 A1* | 8/2011 | Hynecek | H04N 5/335 348/308 |
| 2011/0279719 A1 | 11/2011 | Mabuchi | |
| 2012/0112039 A1* | 5/2012 | Sugano | H04N 5/3532 250/208.1 |
| 2013/0087685 A1* | 4/2013 | Itano | H04N 5/3572 250/208.1 |
| 2013/0265471 A1 | 10/2013 | Abe et al. | |

FOREIGN PATENT DOCUMENTS

| | | | | |
|---|---|---|---|---|
| JP | 2004-343529 A | | 12/2004 | |
| JP | 2008-042347 A | | 2/2008 | |
| JP | 2009-164836 A | | 7/2009 | |
| JP | 2011-010886 | * | 7/2009 | ............ A61B 1/04 |
| JP | 2011-010886 A | | 1/2011 | |

OTHER PUBLICATIONS

Japanese Office Action dated Jun. 30, 2015 issued in JP 2015-512398.

* cited by examiner

IMAGING ELEMENT, IMAGING DEVICE, ENDOSCOPE, ENDOSCOPE SYSTEM, AND METHOD OF DRIVING IMAGING ELEMENT

CROSS-REFERENCE TO RELATED APPLICATIONS

This application is a continuation of PCT international application Ser. No. PCT/JP2014/059270 filed on Mar. 28, 2014 which designates the United States, incorporated herein by reference, and which claims the benefit of priority from Japanese Patent Applications No. 2013-087535, filed on Apr. 18, 2013, incorporated herein by reference.

BACKGROUND OF THE INVENTION

1. Field of the Invention

The present invention relates to an imaging element, an imaging device, an endoscope, an endoscope system, and a method of driving the imaging element.

2. Description of the Related Art

In general, each unit pixel in an imaging device having a CMOS (Complementary Metal-Oxide Semiconductor) imaging element includes at least one photoelectric converter (photodiode), a charge converter, a transfer transistor, a charge converter reset transistor, a pixel source follower transistor, and a pixel output switch transistor.

A charge accumulated in the photoelectric converter is read by the transfer transistor, subjected to voltage conversion by the charge converter, and then output to a vertical transfer line through the pixel source follower transistor and the pixel output switch transistor. Such imaging device performs pixel selection by controlling drive of the pixel output switch transistor.

Various contrivances have been tried in recent years to achieve downsizing of the imaging element. As one of the contrivances, it has been proposed to simplify a pixel configuration by omitting the pixel output switch transistor that configures each unit pixel (e.g., refer to Japanese Patent Application No. 2004-172950).

When a synchronization signal is received from outside to perform pixel selection in an imaging element from which the pixel output switch transistor is omitted, it has been adapted to perform the pixel selection operation upon reception of the synchronization signal from outside and perform a de-selection operation on the selected pixel after reading the selected pixel. It is thus possible that, when the synchronization signal is input at a timing different from a timing at which the synchronization signal is to be input originally, a pixel selected when the synchronization signal is input remains selected and selected while overlapping with a pixel that is newly selected upon reception of the synchronization signal, because the de-selection operation of the pixel being read is not performed properly. As a result, an imaging signal corresponding to at least one frame overlaps, causing a possibility of a frame drop occurring across a plurality of frames.

When such imaging element is used in an endoscope system, the frame drop occurring in such situation may possibly be an obstacle to an observation of a subject.

Moreover, the endoscope system is often used in combination with a device such as an electric knife generating noise, which is in some cases misrecognized as a synchronization signal from outside by the imaging element. When the imaging element is provided at a distal end of an insertion unit of the endoscope and receives the synchronization signal through the insertion unit, for example, the signal is easily affected by the noise generated by the electric knife or the like through the long insertion unit, whereby misrecognition of the synchronization signal due to the disturbance may possibly cause the aforementioned frame drop as well.

There is a need for an imaging element, an imaging device, an endoscope, an endoscope system and a method of driving the imaging element that can prevent a frame drop caused by a synchronization signal input at a timing different from a timing at which the synchronization signal is to be input originally.

SUMMARY OF THE INVENTION

An imaging element according to one aspect of the present invention includes: a plurality of pixels arranged into a two-dimensional matrix, configured to receive light from outside, and configured to generate and output an imaging signal according to an amount of light received; a first transfer line connected to the pixel and configured to transfer the imaging signal; a pixel selection unit configured to perform a selection operation of selecting a selection target pixel from among the plurality of pixels in order to read the imaging signal out to the first transfer line and a de-selection operation of canceling the selection of the pixel being selected; a control unit configured to control the pixel selection unit to perform the selection operation of selecting a new selection target pixel after performing the de-selection operation on the basis of a synchronization signal from outside; and a reference voltage generation unit configured to generate a first voltage and a second voltage lower than the first voltage, wherein the pixel includes: a photoelectric converter configured to perform photoelectric conversion according to the amount of light received and accumulates a charge; a first transfer unit configured to transfer the accumulated charge; a charge converter configured to convert the transferred charge into the imaging signal; a pixel reset unit connected to the reference voltage generation unit and the charge converter and configured to reset the charge converter to the first voltage by supplying the first voltage generated by the reference voltage generation unit; and a pixel amplification transistor including a gate connected to the charge converter, the pixel amplification transistor being connected to the reference voltage generation unit and the first transfer line, being turned on at a time the first voltage is applied to the gate, and being turned off at a time the second voltage is applied to the gate, and wherein the pixel selection unit is configured to perform the selection operation by turning on the pixel amplification transistor of the selection target pixel and perform the de-selection operation that cancels selection of the selected pixel by turning off the pixel amplification transistor of the selected pixel.

A method of driving an imaging element according to another aspect of the present invention is a method of driving an imaging element including: a plurality of pixels arranged into a two-dimensional matrix, configured to receive light from outside, and configured to generate and output an imaging signal according to an amount of light received, each pixel including: a photoelectric converter configured to perform photoelectric conversion according to the amount of light received and accumulates a charge; a first transfer unit configured to transfer the accumulated charge; a charge converter configured to convert the transferred charge into the imaging signal; a pixel reset unit configured to reset the charge converter; and a pixel amplification transistor including a gate connected to the charge converter; and a first transfer line connected to the pixel and configured to transfer the imaging signal, and the method includes: generating a first voltage and a second voltage lower than the first voltage; resetting the charge converter to the first voltage by supplying the first voltage generated; performing a de-selection operation which cancels selection of a selected pixel in order to read the imaging signal out to the first transfer line on the basis of a synchronization signal from outside by turning off the pixel amplification transistor by applying the second voltage to the gate of the pixel amplification transistor; performing a selection operation which selects a selection target pixel from among the plurality of pixels in order to read the imaging signal out to the first transfer line after the de-selection step by turning on the pixel amplification transistor by applying the first voltage to the gate of the pixel amplification transistor; and reading the imaging signal out to the first transfer line from the selected pixel.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
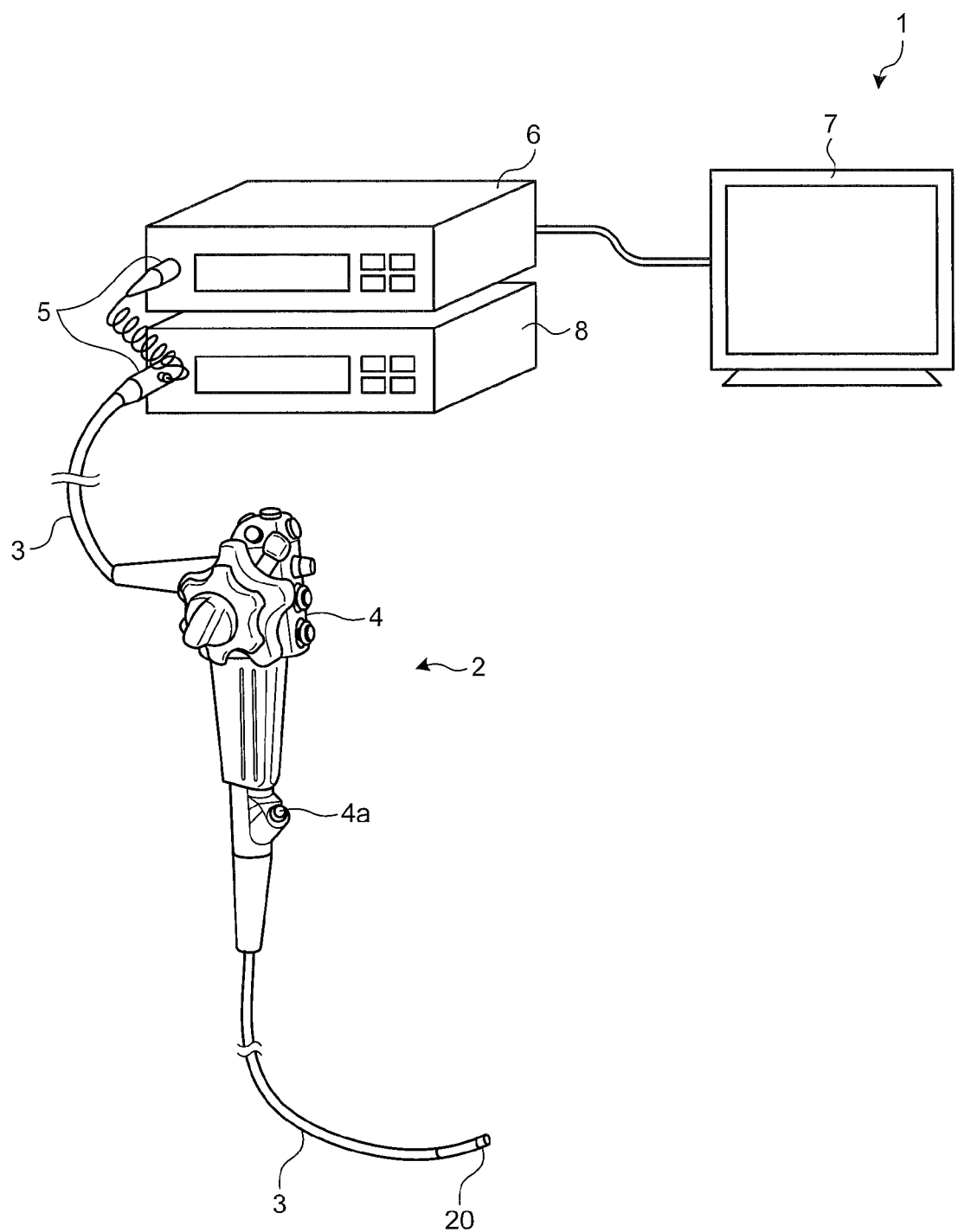
FIG. 1 is a diagram schematically illustrating an overall configuration of an endoscope system according to an embodiment of the present invention.

An endoscope system including an imaging device will be described below as a mode of carrying out the present invention (hereinafter referred to as an "embodiment"). The present invention is not to be limited by the embodiment. Moreover, the same parts among the drawings are assigned the same reference numerals. The drawings being provided schematically, one needs to keep in mind that the relationship between the thickness and width of each member as well as a ratio of each member are different from actual ones. Moreover, the dimension and ratio of some parts are different among the drawings.

FIG. 1 is a diagram schematically illustrating an overall configuration of an endoscope system according to an embodiment of the present invention. An endoscope system 1 illustrated in the diagram includes an endoscope 2, a transmission cable 3, a connector unit 5, a processor (control device) 6, a display device 7, and a light source device 8. The endoscope 2 images an in-vivo image of a subject by inserting an insertion unit being a part of the transmission cable 3 into a body cavity of the subject and outputs an imaging signal. The transmission cable 3 connects the endoscope 2 and the connector unit 5. The connector unit 5 is connected to the endoscope 2, the processor 6 and the light source device 8, performs predetermined signal processing on the imaging signal output by the endoscope 2 connected, and performs analog-digital conversion (A/D conversion) on the imaging signal to output the signal as an image signal. The processor 6 performs predetermined image processing on the image signal output from the connector unit 5 and controls the entire endoscope system 1. The display device 7 displays the image signal processed by the processor 6. The light source device 8 is formed of a white LED, for example. Pulsed white light illuminated by the light source device 8 becomes the illumination light radiated from a distal end side of the insertion unit of the endoscope 2 toward the subject via the connector unit 5 and the transmission cable 3.

The endoscope 2 includes an imaging unit (imaging device) 20 at an end of the transmission cable being the distal end side of the insertion unit inserted into the body cavity of the subject and, at a proximal end side of the insertion unit, includes an operating unit 4 connected to receive various operations against the endoscope 2, the imaging unit imaging an in-vivo image. The operating unit 4 is provided with a treatment tool insertion unit 4a which inserts a treatment tool such as forceps, an electric knife, or an inspection probe into the body cavity of the subject. The imaging unit 20 is connected to the connector unit 5 by the transmission cable 3 through the operating unit 4. An imaging signal of the image captured by the imaging unit 20 is output to the connector unit 5 through the transmission cable 3 that is several meters long, for example.

Figure 2:
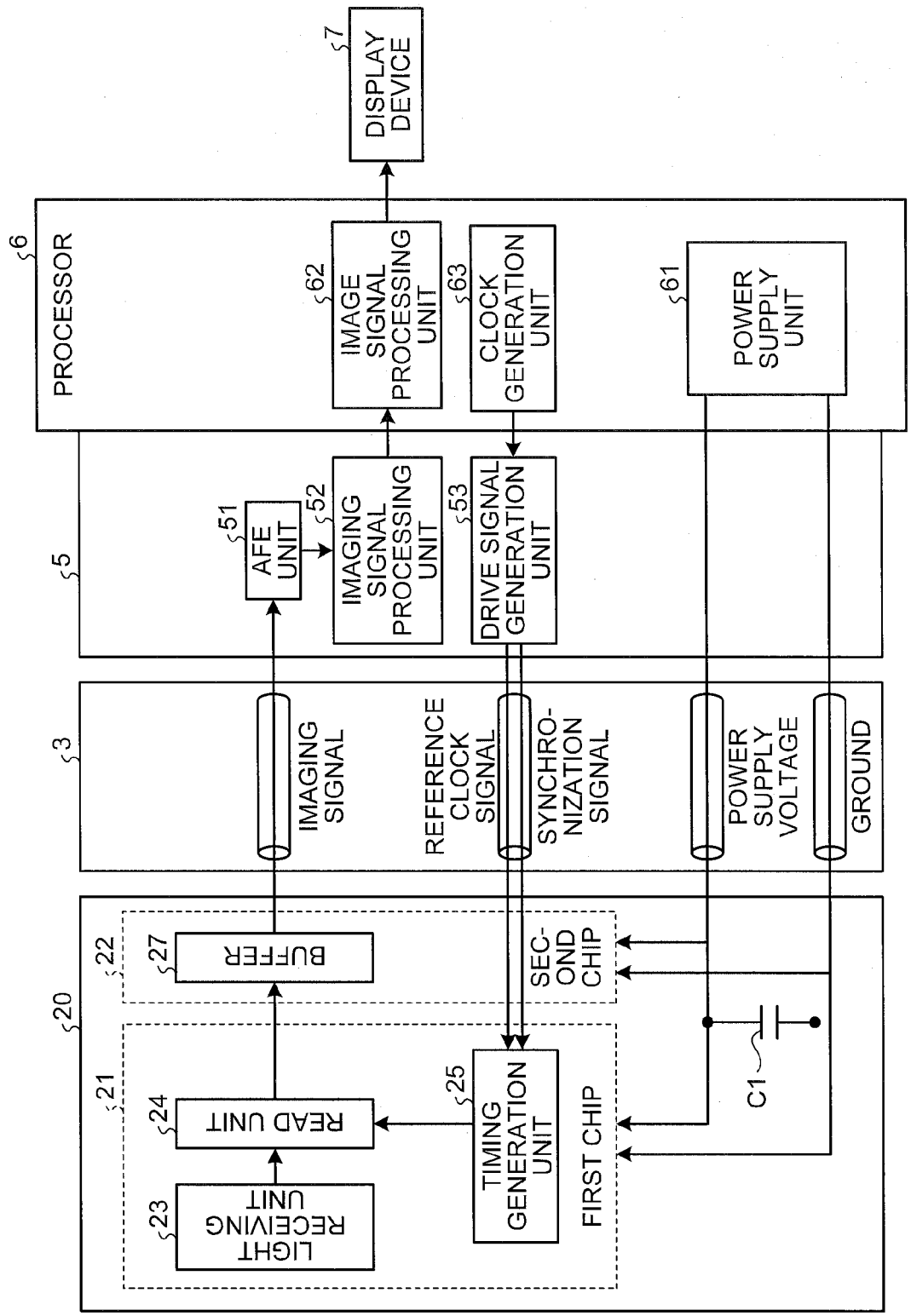
FIG. 2 is a block diagram illustrating a function of a principal part of the endoscope system according to an embodiment of the present invention.

FIG. 2 is a block diagram illustrating a function of a principal part of the endoscope system according to an embodiment of the present invention. Details of each configuration of the endoscope system 1 as well as a path of an electric signal within the endoscope system 1 will be described with reference to FIG. 2.

The imaging unit 20 includes a first chip 21 having a light receiving unit 23 and a second chip 22 having a buffer 27. The first chip 21 and the second chip 22 are stuck facing each other while a space therebetween is connected by a pad arranged at a peripheral portion of the chips or a via passing through the chips. Note that the first chip 21 and the second chip 22 may be not only arranged in a way the principal planes of the chips are parallel with each other but also arranged side by side or in a way one principal plane is perpendicular to the other principal plane depending on the surrounding structure.

The first chip 21 of the imaging unit 20 includes the light receiving unit 23 in which a plurality of unit pixels are arranged into a two-dimensional matrix in a matrix direction, a read unit 24 which reads an imaging signal that is photoelectrically converted by the light receiving unit 23, and a timing generation unit 25 which generates and supplies to the read unit 24 a timing signal on the basis of a reference clock signal and a synchronization signal sent from the connector unit 5. A detailed configuration of the first chip 21 will be described later with reference to FIG. 3.

The second chip 22 of the imaging unit 20 includes the buffer 27 which functions as a transmission unit transmitting only an AC component of the imaging signal output from the first chip 21 to the processor 6 through the transmission cable 3 and the connector unit 5. A combination of circuits mounted on the first chip 21 and the second chip 22 can be modified as appropriate according to the design.

The imaging unit 20 also receives a power supply voltage (VDD) generated by a power supply unit 61 of the processor 6 along with ground (GND) through the transmission cable 3. A capacitor C1 for stabilizing power supply is provided between the power supply voltage (VDD) and the ground (GND) supplied to the imaging unit 20.

The connector unit 5 includes an analog front end (AFE) unit 51, an imaging signal processing unit 52, and a drive signal generation unit 53. The connector unit 5 electrically connects the endoscope 2 (imaging unit 20) and the processor 6 and functions as a relay processing unit that relays an electric signal. The connector unit 5 and the imaging unit 20 are connected by the transmission cable 3, whereas the connector unit 5 and the processor 6 are connected by a coil cable, for example. The connector unit 5 is also connected to the light source device 8.

The AFE unit 51 receives the imaging signal transmitted from the imaging unit 20, performs impedance matching by using a passive element such as a resistor, extracts an AC component with the capacitor, and then determines an operating point with a partial resistor. After that, the AFE unit 51 performs analog-digital (A/D) conversion on the analog imaging signal and transmits the signal as a digital imaging signal to the imaging signal processing unit 52.

The imaging signal processing unit 52 is formed of an FPGA (Field Programmable Gate Array), for example, and performs predetermined signal processing such as noise removal against the digital imaging signal input from the AFE unit 51.

The drive signal generation unit 53 generates the synchronization signal indicating a start position of each frame on the basis of the reference clock signal (such as a 27 MHz clock) which is supplied from the processor 6 and serves as a reference of operation in each component of the endoscope 2, and then outputs the synchronization signal along with the reference clock signal to the timing generation unit 25 of the imaging unit 20 through the transmission cable 3, or the insertion unit being a part of the transmission cable 3. The synchronization signal generated here includes a horizontal synchronization signal and a vertical synchronization signal and is coded. The horizontal synchronization signal and the vertical synchronization signal are output as is when the timing generation unit 25 of the imaging unit 20 does not have a function which decodes the synchronization signal. The synchronization signal is coded before output to allow the horizontal synchronization signal and the vertical synchronization signal to be transmitted on the same signal line and thus to be able to reduce the number of signal lines within the transmission cable 3.

The processor 6 includes the power supply unit 61, an image signal processing unit 62, and a clock generation unit 63 and functions as a control device controlling the entire endoscope system 1. The power supply unit 61 generating the power supply voltage (VDD) supplies the generated power supply voltage along with the ground (GND) to the imaging unit 20 through the connector unit 5 and the transmission cable 3. The image signal processing unit 62 performs predetermined image processing on the digital imaging signal, on which the signal processing such as noise removal is performed by the imaging signal processing unit 52, converts the signal into an image signal, and outputs it to the display device 7. The clock generation unit 63 outputs the reference clock signal to the drive signal generation unit 53.

The display device 7 displays the image captured by the imaging unit 20 on the basis of the image signal. The image processing performed in the image signal processing unit 62 includes synchronization processing, white balance (WB) adjustment processing, gain adjustment processing, gamma correction processing, digital-analog (D/A) conversion processing, and format conversion processing, for example.

Figure 3:
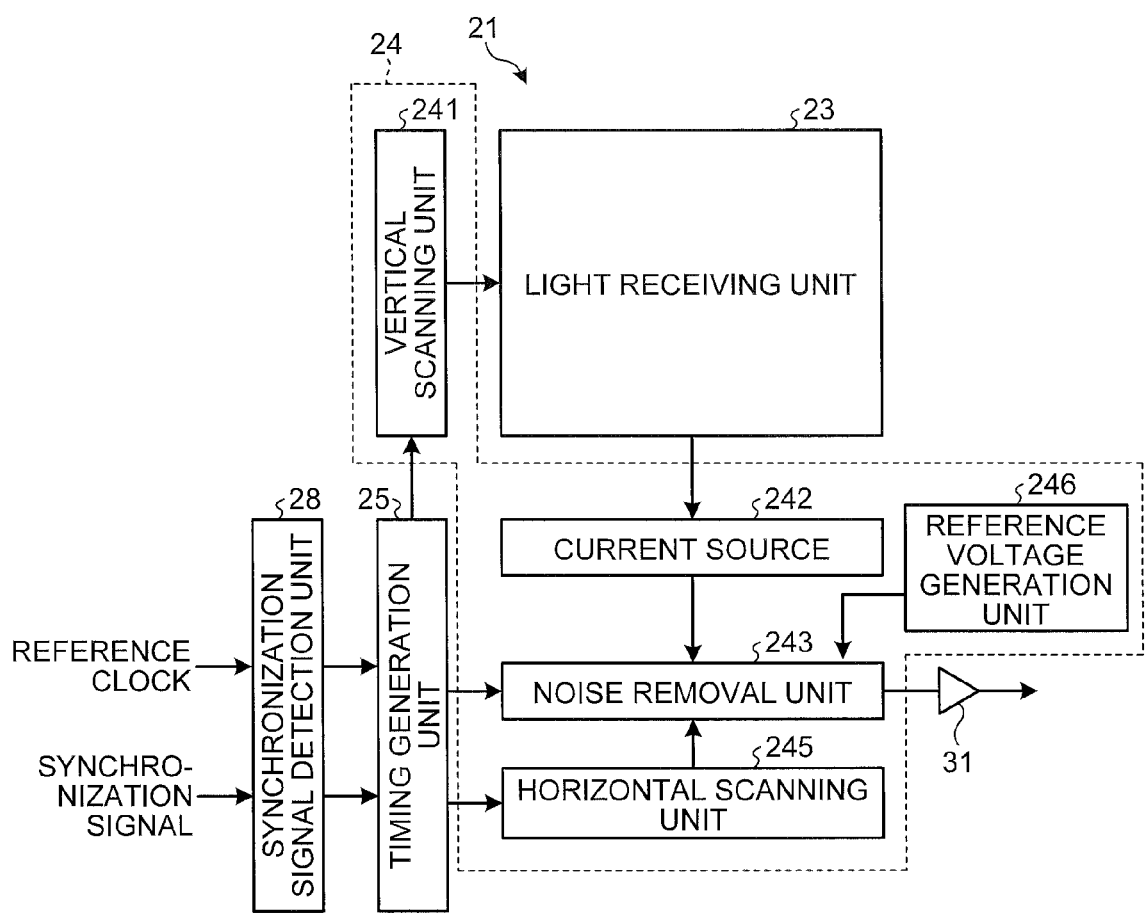
FIG. 3 is a block diagram illustrating details of a first chip illustrated in FIG. 2.
Figure 4:
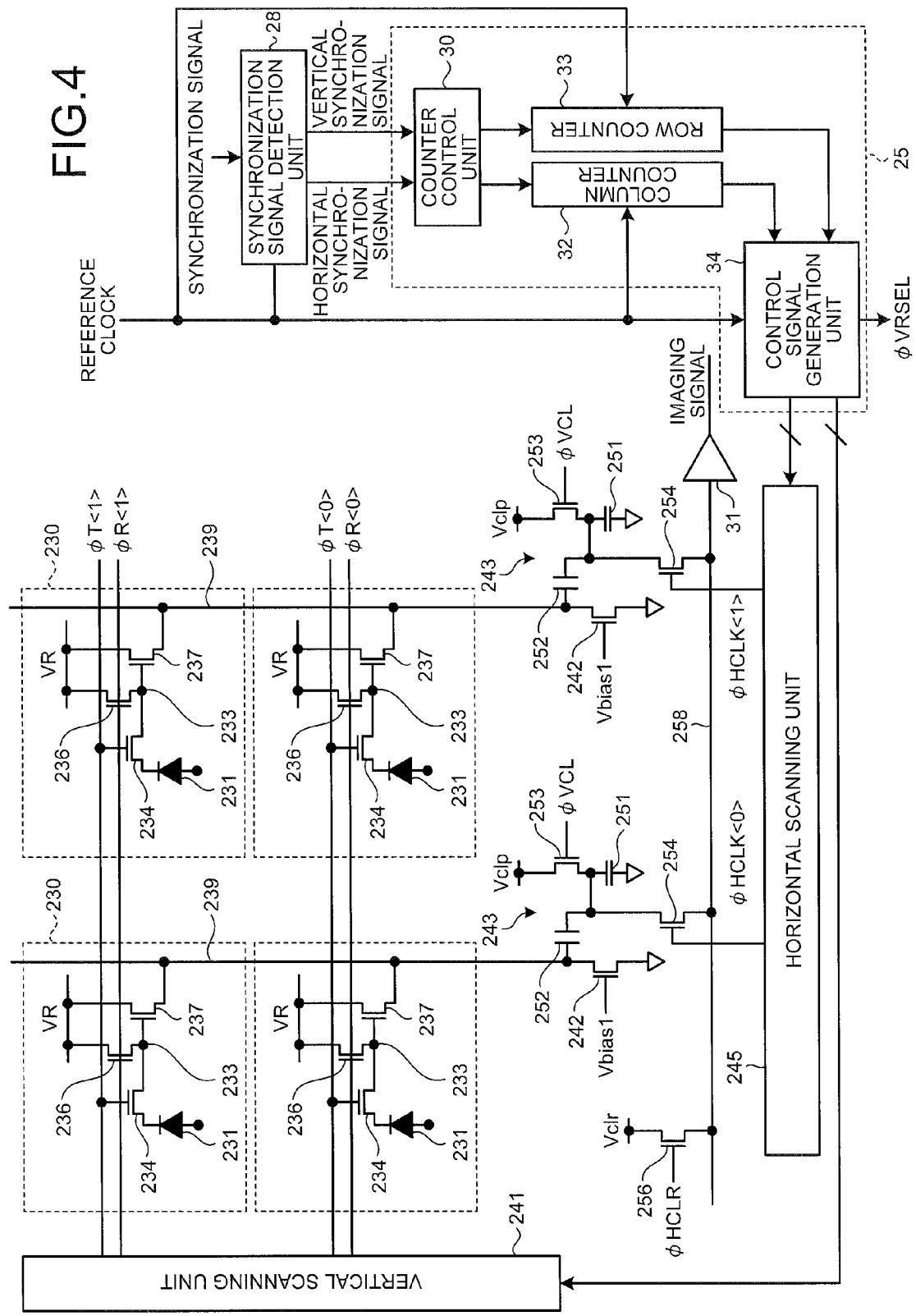
FIG. 4 is a schematic diagram illustrating a configuration of the first chip of the endoscope system according to an embodiment.

FIG. 3 is a block diagram illustrating the detailed configuration of the first chip illustrated in FIG. 2. FIG. 4 is a schematic diagram illustrating the configuration of the first chip of the endoscope system according to an embodiment. The light receiving unit 23, the read unit (drive unit) 24, the timing generation unit 25, and a synchronization signal detection unit 28 are mounted to the first chip 21, for example.

The synchronization signal detection unit 28 receives the reference clock signal and the coded synchronization signal from the connector unit 5, decodes the coded synchronization signal, and outputs the decoded horizontal synchronization signal and vertical synchronization signal to the timing generation unit 25.

The timing generation unit 25 includes a counter control unit 30, a column counter 32, a row counter 33, and a control signal generation unit 34. The timing generation unit 25 generates various drive signals (such as φT, φR, φVCL, φHCLR, φHCLK, and φVRSEL) on the basis of the reference clock signal from the connector unit 5 as well as the horizontal synchronization signal and vertical synchronization signal from the synchronization signal detection unit 28, and supplies the signals to a vertical scanning unit 241, a noise removal unit 243, a horizontal scanning unit 245, and a reference voltage generation unit 246.

The counter control unit 30 outputs a reset signal to the column counter 32 on the basis of the reference clock signal and the horizontal synchronization signal. The counter control unit 30 further outputs a reset signal to the row counter 33 on the basis of the reference clock signal and the vertical synchronization signal. Moreover, the counter control unit 30 monitors a column counter value of the column counter 32, and when the value reaches a predetermined counter value, outputs a count up signal to the row counter 33.

The column counter 32 counts up the column counter value every predetermined period on the basis of the reference clock signal. The column counter value is output to the control signal generation unit 34. The column counter 32 resets the column counter value when the reset signal is input from the counter control unit 30.

The row counter 33 counts up a row counter value on the basis of the reference clock signal and the count up signal input from the counter control unit 30. The row counter value is output to the control signal generation unit 34. The row counter 33 resets the row counter value when the reset signal is input from the counter control unit 30.

The control signal generation unit 34 generates the drive signal (such as φHCLK) on the basis of the reference clock signal and the column counter value, applies a column shift pulse to the signal and outputs it to the horizontal scanning unit 245. The control signal generation unit 34 also generates the drive signals (such as φT and φR) on the basis of the reference clock signal and the row counter value, applies a row shift pulse to the signal and outputs it to the vertical scanning unit 241. Moreover, the control signal generation unit generates the drive signals (such as φVCL, φHCLR, and φVRSEL) on the basis of the reference clock signal, the horizontal synchronization signal and the vertical synchronization signal, and outputs the signals to the noise removal unit 243, a horizontal reset transistor 256, and the reference voltage generation unit 246, respectively.

The read unit 24 includes the vertical scanning unit (row selector) 241, a current source 242, the noise removal unit 243, the horizontal scanning unit (column selector) 245, and the reference voltage generation unit 246.

The vertical scanning unit 241 applies row selection pulses φT <M> and φR <M> to a selected row <M> (M=0, 1, 2, ..., m−1, m) of the light receiving unit 23 on the basis of the drive signals (φT and φR) supplied from the timing generation unit 25, so that each unit pixel 230 of the light receiving unit 23 is driven by the current source 242, and the imaging signal as well as a noise signal generated in resetting a pixel are transferred to a vertical transfer line (first transfer line) 239 and then output to the noise removal unit 243.

The noise removal unit 243 removes output variations for each unit pixel 230 as well as the noise signal generated in resetting a pixel, and outputs an imaging signal that is photoelectrically converted in each unit pixel 230. The noise removal unit 243 will be described in detail later on.

The horizontal scanning unit 245 applies a column selection pulse φHCLK <N> to a selected column <N> (N=0, 1, 2, ..., n−1, n) of the light receiving unit 23 on the basis of the drive signal (φHCLK) supplied from the timing generation unit 25, transfers an imaging signal that is photoelectrically converted in each unit pixel 230 to a horizontal transfer line (second transfer line) 258 through the noise removal unit 243, and outputs the signal to an output unit 31.

A number of unit pixels 230 are arranged into the two-dimensional matrix in the light receiving unit 23 of the first chip 21. Each unit pixel 230 includes a photoelectric converter (photodiode) 231, a charge converter 233, a transfer transistor (first transfer unit) 234, a pixel reset unit (transistor) 236, and a pixel source follower transistor 237. Note that in the present description, one or a plurality of photoelectric converters and the transfer transistor transferring a signal charge from the photoelectric converters to the charge converter 233 are called as a unit cell. That is, the unit cell includes a set of one or a plurality of the photoelectric converters and the transfer transistor, where one unit cell is included in each unit pixel 230.

While the unit cell is formed of one photoelectric converter without performing pixel sharing in the present embodiment, the unit cell may also be formed of the plurality of photoelectric converters as one set. In this case, for example, the unit cell may be formed of two photoelectric converters adjacent to each other in the column direction as one set, two photoelectric converters adjacent to each other in the row direction as one set, or four photoelectric converters adjacent to one another in the row and column directions as one set.

The photoelectric converter 231 photoelectrically converts an incident light into an amount of signal charge corresponding to the amount of light, and accumulates the charge. A cathode side of the photoelectric converter 231 is connected to one end side of the transfer transistor 234, while an anode side of the photoelectric converter is connected to the ground GND. The charge converter 233 is formed of a floating diffusion capacitor (FD) and converts the charge accumulated in the photoelectric converter 231 into voltage.

The transfer transistor 234 transfers the charge from the photoelectric converter 231 to the charge converter 233. A gate of the transfer transistor 234 is connected to a signal line to which a drive pulse (row selection pulse) φT is supplied, while another end side of the transistor is connected to the charge converter 233. When the drive signal φT is supplied from the vertical scanning unit 241 through the signal line, the transfer transistor 234 is turned on so that the signal charge is transferred from the photoelectric converter 231 to the charge converter 233.

The pixel reset unit (transistor) 236 resets the charge converter 233 to a predetermined potential. The pixel reset unit 236 is connected to a variable voltage VR at one end side, the charge converter 233 at another end side, and a signal line to which the drive signal φR is supplied at a gate. The pixel reset unit 236 is turned on when the drive signal φR is supplied thereto from the vertical scanning unit 241 through the signal line, so that the charge converter 233 discharges the signal charge accumulated therein and is then reset to a predetermined potential.

The pixel source follower transistor (pixel amplification unit) 237 is connected to the variable voltage VR at one end side and the vertical transfer line 239 at another end side. Input to a gate of the transistor is a signal (imaging signal or a signal at the time of resetting) on which voltage conversion is performed by the charge converter 233. When the drive signal φT is supplied to a gate of the transfer transistor 234 following a selection operation (to be described), a charge is read from the photoelectric converter 231, subjected to voltage conversion by the charge converter 233, and then transferred to the vertical transfer line 239 through the pixel source follower transistor 237.

In the present embodiment, the pixel source follower transistor 237 is turned on once the drive signal φR is supplied to the gate of the pixel reset unit 236 when the variable voltage VR is at the level of the power supply voltage VDD (such as 3.3 V), and a unit pixel including the pixel reset unit 236 is selected (selection operation). The pixel source follower transistor 237 is turned off once the drive signal φR is supplied to the gate of the pixel reset unit 236 when the variable voltage VR is at the level of a de-selection voltage Vfd_L (such as 1 V), and the selection of the unit pixel including the pixel reset unit 236 is canceled (de-selection operation).

The current source 242 is connected to the vertical transfer line 239 at one end side and the ground GND at another end side, and a bias voltage Vbias1 is applied to a gate of the current source. The unit pixel 230 is driven by the current source 242, and the output of the unit pixel 230 is read out to the vertical transfer line 239. The signal read out to the vertical transfer line 239 is input to the noise removal unit 243.

The noise removal unit 243 includes an AC coupling capacitor (transfer capacitor) 252 connected to the vertical transfer line 239 at one end side, a charge accumulating capacitor (sample capacitor) 251 connected between another end side of the transfer capacitor 252 and the ground, and a potential clamp transistor (clamp switch) 253 connected to a connection node between the transfer capacitor 252 and the sample capacitor 251. Note that the connection node is connected to one end side of a column selection switch 254.

When the drive signal ϕR is supplied to the gate of the pixel reset unit 236 while the variable voltage VR is at the level of the power supply voltage VDD, a noise signal is read out to the vertical transfer line 239 and transmitted by the transfer capacitor 252. When the drive signal ϕVCL is thereafter input from the timing generation unit 25 to a gate of the clamp switch 253, a noise signal level is sampled to the sample capacitor 251 through the clamp switch 253 (by turning off the clamp switch 253 that is turned on). After that, an imaging signal (light-noise sum signal) including the noise signal is transmitted by the transfer capacitor 252 again when the imaging signal is read. The change in voltage of the imaging signal after resetting the pixel is transmitted, whereby an imaging signal obtained by subtracting the noise signal from the light-noise sum signal can be extracted as a result.

The horizontal reset transistor 256 is connected to a horizontal reset voltage Vclr at one end side and a horizontal transfer line 258 at another end side. The drive signal ϕHCLR from the timing generation unit 25 is input to a gate of the horizontal reset transistor 256. When the drive signal ϕHCLR from the timing generation unit 25 is input to the gate of the horizontal reset transistor 256, the horizontal reset transistor 256 is turned on while the horizontal transfer line 258 is reset.

One end side of the column selection switch 254 is connected to the other end side of the transfer capacitor 252 through the connection node between the transfer capacitor 252 and the sample capacitor 251, while another end side of the column selection switch is connected to the horizontal transfer line (second transfer line) 258. A signal line provided to supply the drive signal ϕHCLK <N> from the horizontal scanning unit 245 is connected to a gate of the column selection switch 254. When the drive signal ϕHCLK <N> is supplied from the horizontal scanning unit 245 to the gate of the column selection switch 254 in a column <N>, the column selection switch 254 is turned on while a signal (the imaging signal from which the noise is removed by the noise removal unit 243) of the vertical transfer line 239 in the column <N> is transferred to the horizontal transfer line 258.

The signal read out to the horizontal transfer line 258 is input to the output unit 31. The output unit 31 amplifies, as needed, the imaging signal from which the noise is removed and outputs the signal to the second chip 22.

In the second chip 22, the imaging signal from which the noise is removed is transmitted to the connector unit 5 through the transmission cable 3.

Figure 5:
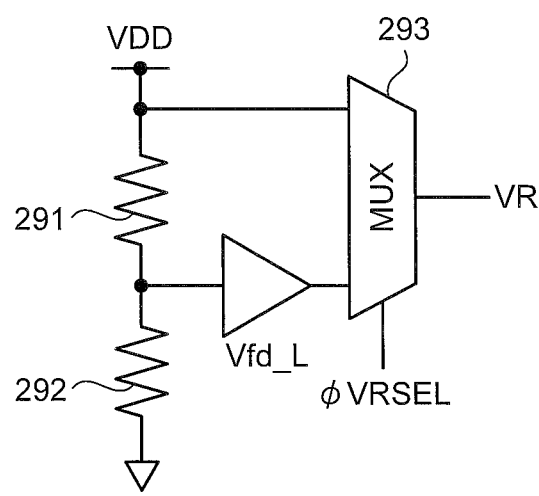
FIG. 5 is a schematic diagram illustrating a configuration of a reference voltage generation unit of the endoscope system according to an embodiment.

FIG. 5 is a schematic diagram illustrating a configuration of the reference voltage generation unit of the light receiving unit in the endoscope system according to an embodiment. The reference voltage generation unit (constant voltage signal generation unit) 246 includes a resistor divider formed of two resistors 291 and 292, and a multiplexer 293 driven by the drive signal ϕVRSEL.

The multiplexer 293 applies the variable voltage VR to all pixels while alternately switching the voltage between the power supply voltage VDD and the de-selection voltage Vfd_L generated in the resistor divider, in accordance with the drive signal ϕVRSEL input from the timing generation unit 25.

Figure 6:
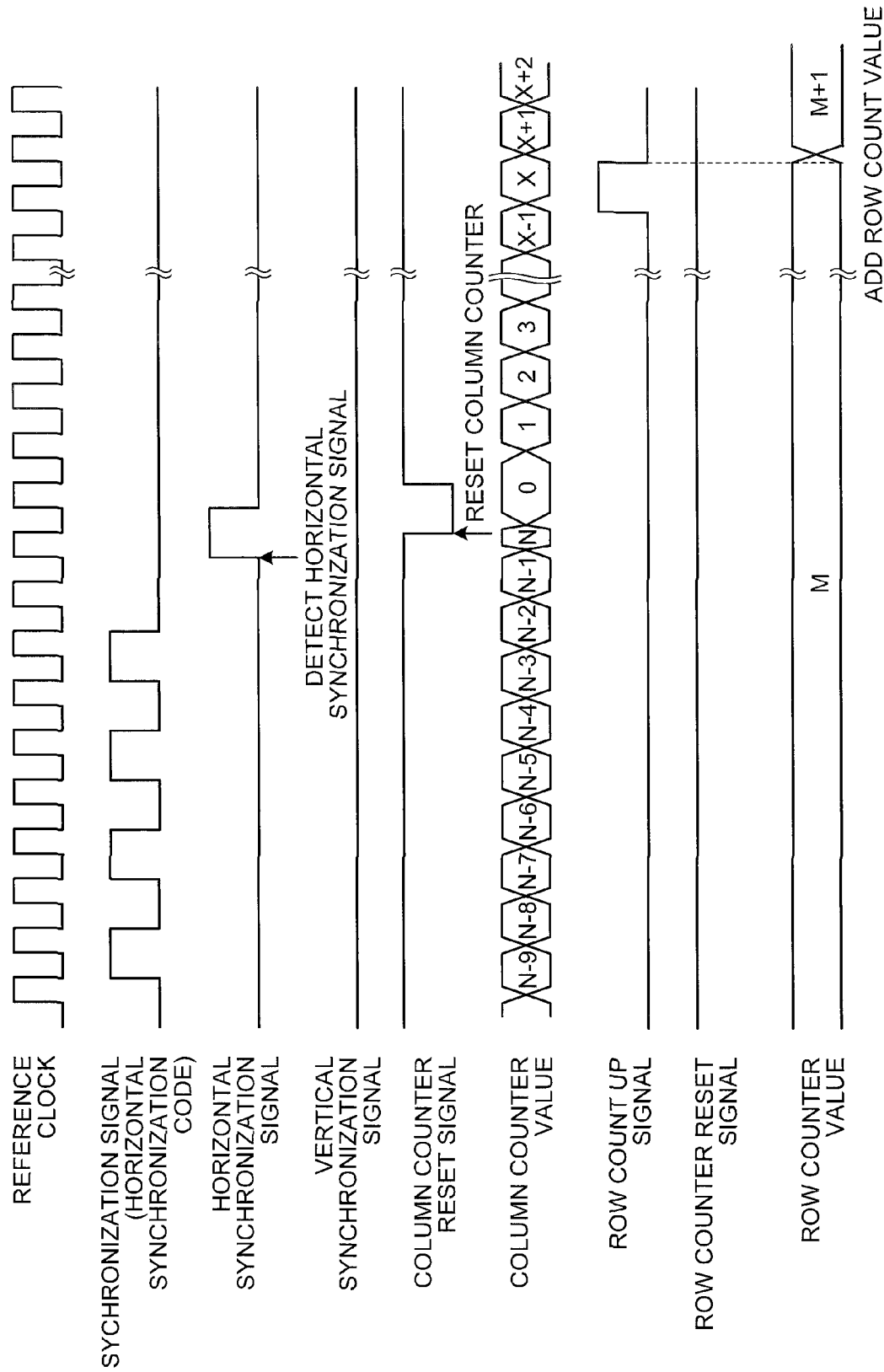
FIG. 6 is a timing chart illustrating an operation when a horizontal synchronization signal is detected by a timing generation unit according to an embodiment.

FIG. 6 is a timing chart illustrating an operation when the horizontal synchronization signal is detected by the timing generation unit 25 according to an embodiment.

The timing chart illustrates from the top the reference clock signal, a coded synchronization signal (horizontal synchronization code), a decoded horizontal synchronization signal, a decoded vertical synchronization signal (frame synchronization signal), a column counter reset signal, a column counter value, a row count up signal, a row counter reset signal, and a row counter value.

When the reference clock signal and the coded synchronization signal (horizontal synchronization code) are input to the timing generation unit 25 from outside, the synchronization signal detection unit 28 decodes the synchronization signal and detects the horizontal synchronization signal. The synchronization signal detection unit 28 outputs the detected horizontal synchronization signal to the counter control unit 30. Receiving the horizontal synchronization signal, the counter control unit 30 outputs the column counter reset signal to the column counter 32. Upon receiving the column counter reset signal, the column counter 32 resets the column counter value at the fall of the column counter reset signal. Moreover, the counter control unit 30 monitors the column counter value and, when the column counter value reaches a predetermined value ("X" in the chart), outputs the row count up signal to the row counter 33. Upon receiving the row count up signal, the row counter 33 counts up the row count value at the rise of the row count up signal.

Figure 7:
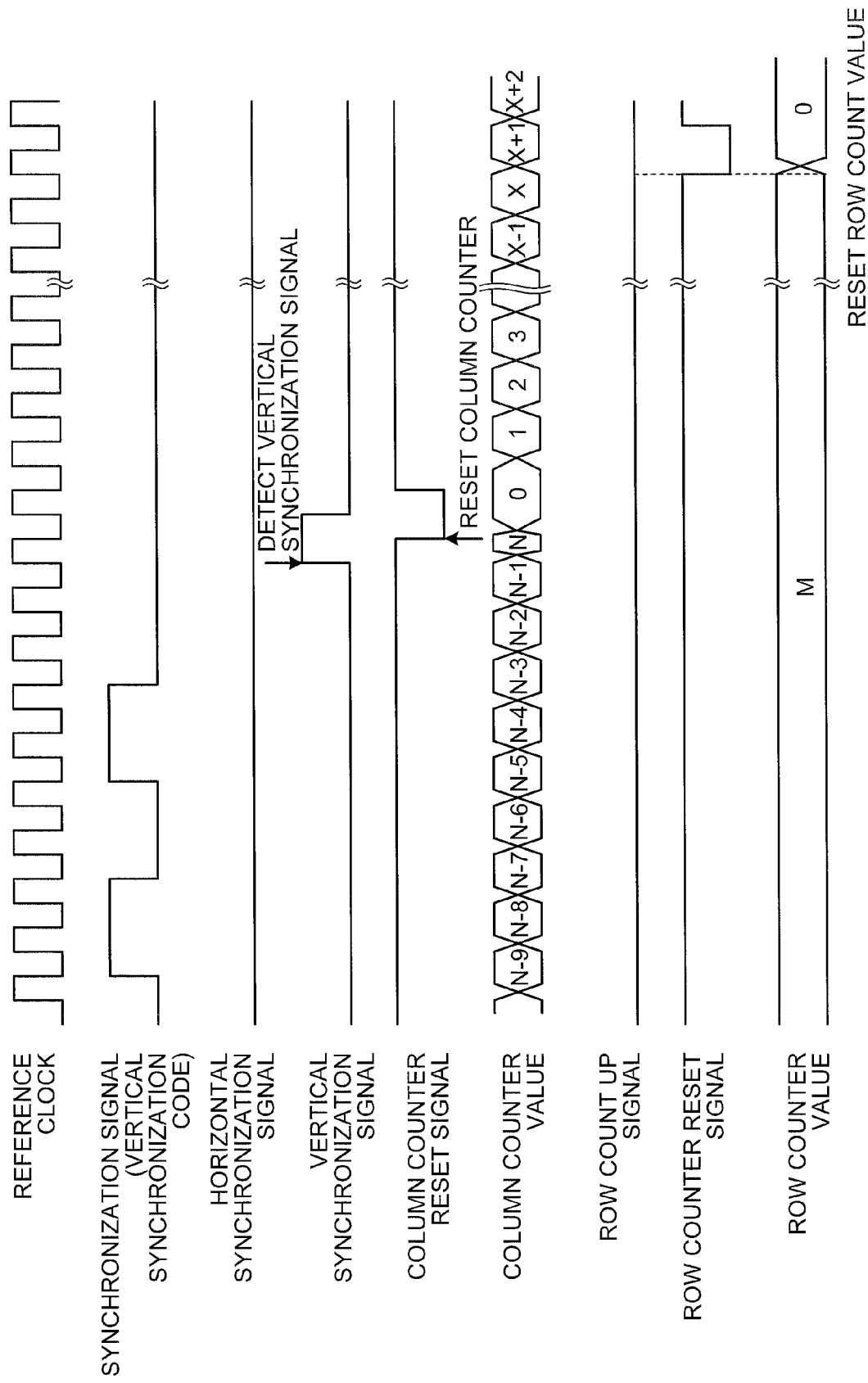
FIG. 7 is a timing chart illustrating an operation when a vertical synchronization signal is detected by the timing generation unit according to an embodiment.

FIG. 7 is a timing chart illustrating an operation when the vertical synchronization signal is detected by the timing generation unit 25 according to an embodiment.

The timing chart illustrates from the top the reference clock signal, a coded synchronization signal (vertical synchronization code), the decoded horizontal synchronization signal, the decoded vertical synchronization signal (frame synchronization signal), the column counter reset signal, the column counter value, the row count up signal, the row counter reset signal, and the row counter value.

When the reference clock signal and the coded synchronization signal (vertical synchronization code) are input to the timing generation unit 25 from outside, the synchronization signal detection unit 28 decodes the synchronization signal and detects the vertical synchronization signal. The synchronization signal detection unit 28 outputs the detected vertical synchronization signal to the counter control unit 30. Receiving the vertical synchronization signal, the counter control unit 30 outputs the column counter reset signal to the column counter 32. Upon receiving the column counter reset signal, the column counter 32 resets the column counter value at the fall of the column counter reset signal. Moreover, the counter control unit 30 monitors the column counter value and, when the column counter value reaches the predetermined value ("X" in the chart), outputs the row counter reset signal to the row counter 33. Upon receiving the row counter reset signal, the row counter 33 resets the row count value at the fall of the row counter reset signal. Therefore, when the vertical synchronization signal is detected, the column counter value is reset first, and then the row counter value is reset after a predetermined cycle.

Figure 8:
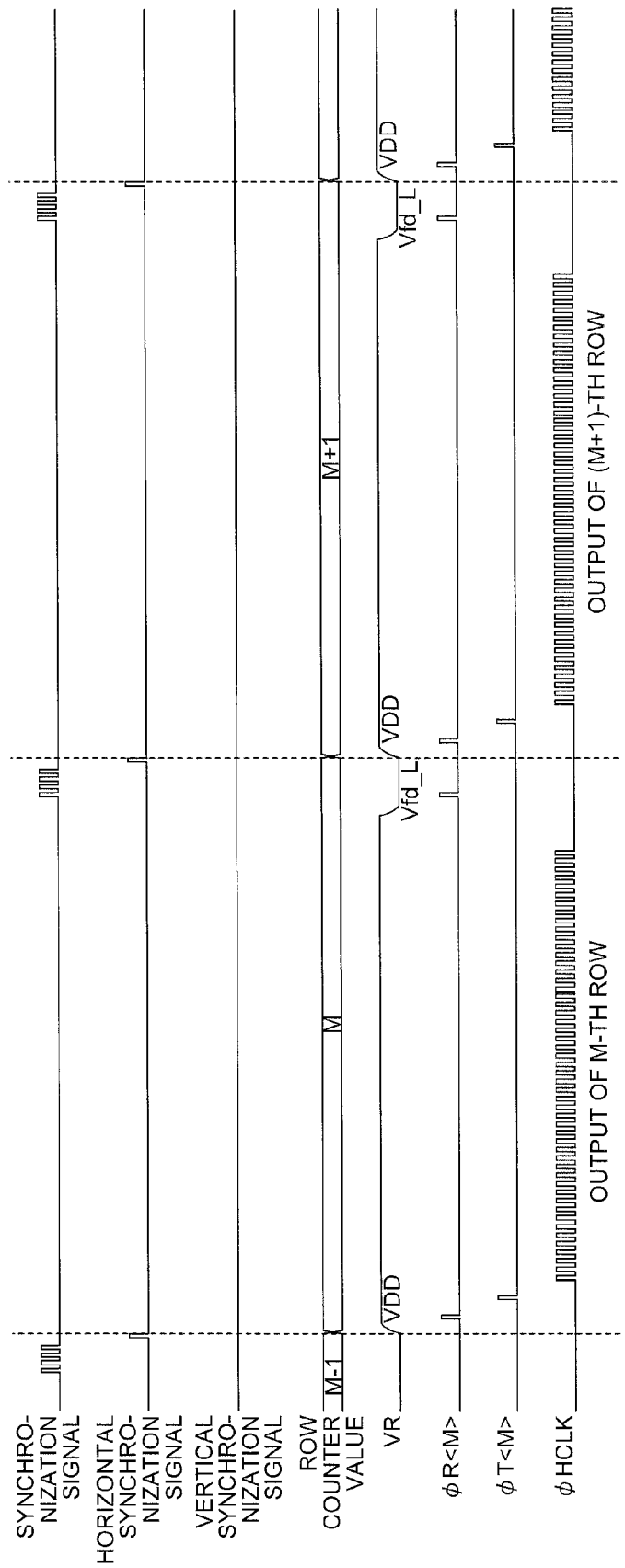
FIG. 8 is a timing chart illustrating a driving timing of an imaging device in normal time according to a variation.

FIG. 8 is a timing chart illustrating a driving timing of an imaging device in normal time according to a variation. In this variation, a conventional driving method is applied to the imaging device of the embodiment. The timing chart illustrates from the top a synchronization signal input from outside, a detected horizontal synchronization signal, a detected vertical synchronization signal, a row counter value, a variable voltage VR, a drive signal φR <M>, a drive signal φT <M>, and a drive signal φHCLK.

First, the horizontal synchronization signal is detected upon input of the synchronization signal so that the row counter value is counted up from "M−1" to "M" at the fall of the horizontal synchronization signal. At the same time, the variable voltage VR is set to the level of VDD (such as 3.3 V).

Next, the pulsed drive signal φR <M> is applied to the gate of the pixel reset unit 236 in a pixel row <M> while the variable voltage VR is set to the level of VDD. The power supply voltage VDD is thus applied to the gate of the pixel source follower transistor 237 in the pixel row <M>, thereby turning on the pixel source follower transistor 237. The unit pixel 230 included in the pixel row <M> is selected in this manner (selection operation).

At the same time, a variation distinctive of the unit pixel 230 to be read and a noise signal including noise generated in resetting a pixel are output from the unit pixel 230 to the vertical transfer line 239. The noise signal level is sampled to the sample capacitor 251 by switching the clamp switch 253 from on (high φVCL) to off (low φVCL).

After that, the pulsed drive signal φT <M> is applied to the gate of the transfer transistor 234 in the pixel row <M> while the variable voltage VR is set to the level of VDD. The charge that is photoelectrically converted by the photoelectric converter 231 is subjected to voltage conversion by the charge converter 233, so that a signal after subjected to the voltage conversion is read out to the vertical transfer line 239. The pixel output switch being omitted, the imaging signal (light-noise sum signal) subjected to the voltage conversion by the charge converter 233 is transferred to the vertical transfer line 239 through the pixel source follower transistor 237 and input to the noise removal unit 243. The noise removal unit 243 outputs an imaging signal (optical signal) by subtracting the noise signal sampled to the sample capacitor 251 from the imaging signal (light-noise sum signal).

Then, the horizontal scanning unit 245 successively applies a column selection pulse φHCLK <N> to a selected column <N> (N=0, 1, 2, ..., n−1, n) of the light receiving unit 23 on the basis of the drive signal (φHCLK) supplied from the timing generation unit 25, transfers the imaging signal that is photoelectrically converted in each unit pixel 230 to the horizontal transfer line 258 through the noise removal unit 243, and outputs the signal to the output unit 31.

Once the imaging signal is transferred to the horizontal transfer line 258, or the column counter value (FIG. 6) is counted up to a maximum value (n), the variable voltage VR is set to the level of Vfd_L (such as 1 V).

After that, the pulsed drive signal φR <M> is applied to the gate of the pixel reset unit 236 in the pixel row <M> while the variable voltage VR is set to the level of Vfd_L. The de-selection voltage Vfd_L is thus applied to the gate of the pixel source follower transistor 237 in the pixel row <M>, thereby turning off the pixel source follower transistor 237. The selection of the unit pixel 230 included in the pixel row <M> is canceled in this manner (de-selection operation).

After that, the aforementioned processing is repeated when a next synchronization signal is input. In other words, upon input of the synchronization signal, this variation in normal operation successively performs the counting up of the row counter value, the selection operation of the pixel row, the operation of reading the imaging signal from the selected pixel row, and the de-selection operation of the selected pixel row.

Figure 9:
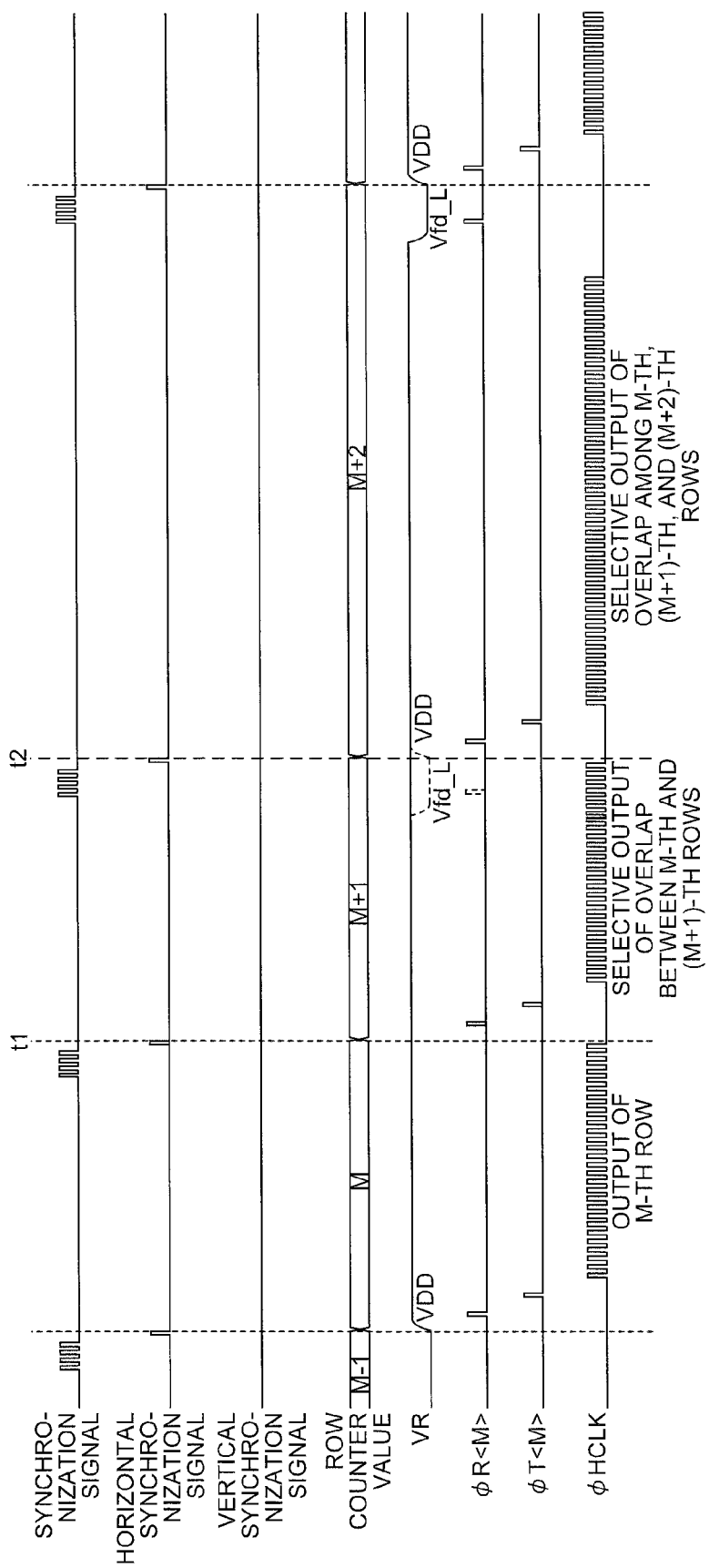
FIG. 9 is a timing chart illustrating a driving timing when a horizontal synchronization signal is input to the imaging device at a timing different from a normal timing, according to a variation.

FIG. 9 is a timing chart illustrating a driving timing when the horizontal synchronization signal is input to the imaging device at a timing different from a normal timing, according to a variation. Similar to FIG. 8, the timing chart illustrates from the top a synchronization signal input from outside, a detected horizontal synchronization signal, a detected vertical synchronization signal, a row counter value, a variable voltage VR, a drive signal φR <M>, a drive signal φT <M>, and a drive signal φHCLK.

While the synchronization signal is input at a predetermined cycle in normal operation, there is a case where the synchronization signal is erroneously input at an unintended timing different from the predetermined cycle due to disturbance caused by an electric knife or the like. FIG. 9 illustrates the operation when the synchronization signal is input at the unintended timing.

When misrecognition of the horizontal synchronization signal occurs due to the disturbance in the middle of the read operation performed after selection of the unit pixel 230 in the pixel row <M> (timing t1), for example, the column counter value (FIG. 6) is not yet counted up to a maximum value (n) so that the counting up of the row counter value, the selection operation of a pixel row <M+1>, and the operation of reading the imaging signal from the unit pixel 230 in the pixel row <M+1> are performed without performing the de-selection operation of the unit pixel 230 in the pixel row <M>. As the de-selection operation of the unit pixel 230 in the pixel row <M> (application of the drive signal φR <M> while VR is set to the level of Vfd_L as indicated with a dashed line in the timing chart) is not performed, the imaging signal read at this time is the overlap of the imaging signals from the unit pixels 230 in the pixel row <M> and the pixel row <M+1>.

Moreover, the normal synchronization signal is input at the predetermined cycle so that, even when the misrecognition of the synchronization signal occurs due to the disturbance, a normal synchronization signal is input a predetermined time after the input of the previous synchronization signal (timing t2). The input of the normal synchronization signal at the timing t2 is performed before completion of the read operation of the pixel row <M+1> that is initiated by the misrecognition of the synchronization signal caused by the disturbance, so that the counting up of the row counter value, the selection operation of a pixel row <M+2>, and the operation of reading the imaging signal from the unit pixel 230 in the pixel row <M+2> are performed without performing the de-selection operation of the unit pixel 230 in the pixel row <M+1> that is selected by the misrecognition of the synchronization signal due to the disturbance. As the de-selection operation of the unit pixel 230 in each of the pixel rows <M> and <M+1> is not performed, the imaging signal read at this time is the overlap of the imaging signals of the unit pixels 230 in the pixel rows <M>, <M+1> and <M+2>.

The reading of the unit pixel 230 in the pixel row <M+2> is initiated by the synchronization signal input at a normal timing, so that the de-selection operation of the unit pixel 230 in the pixel row <M+2> is performed before a new synchronization signal is input. The row counter value being "M+2", however, the drive signal φR is not applied to the pixel reset unit 236 included in the pixel rows <M> and <M+1> while this frame is being read, whereby the imaging signals from these two rows overlap with an imaging signal of another pixel row while this frame is being read. Moreover, the imaging signals from the pixel rows <M> and <M+1> overlap in a next frame as well until the de-selection operation is performed on each of these selected pixel rows after completing the read operation for each row.

Accordingly, in this variation, there occurs the overlap of the imaging signals at least in the frame being read and the following frame when the horizontal synchronization signal is input at a timing different from the normal timing, whereby a so-called frame drop occurs across a plurality of frames.

Figure 10:
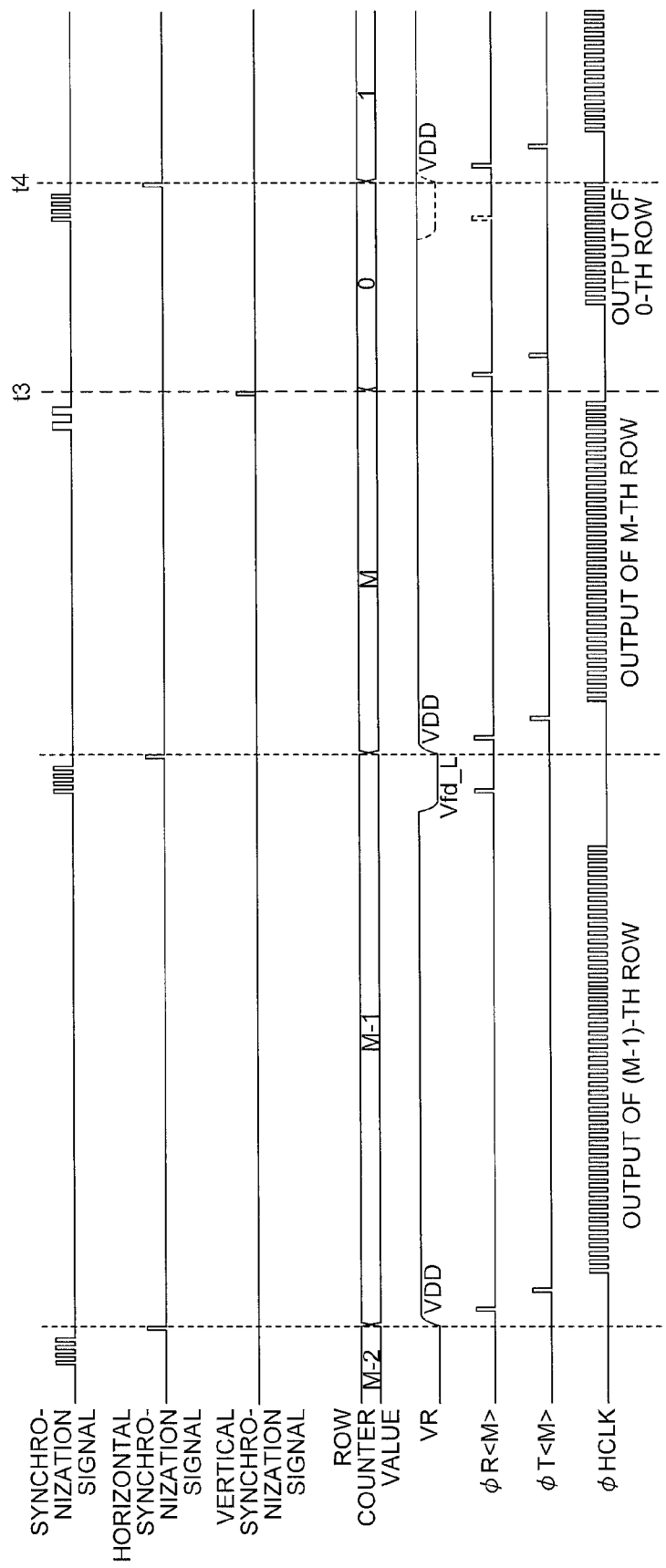
FIG. 10 is a timing chart illustrating a driving timing when a vertical synchronization signal is input to the imaging device at a timing different from a normal timing, according to a variation.

FIG. 10 is a timing chart illustrating a driving timing when the vertical synchronization signal is input to the imaging device at a timing different from a normal timing, according to a variation. Similar to FIG. 8, the timing chart illustrates from the top a synchronization signal input from outside, a detected horizontal synchronization signal, a detected vertical synchronization signal, a row counter value, a variable voltage VR, a drive signal φR <M>, a drive signal φ<M>, and a drive signal φHCLK. FIG. 10 illustrates the operation when the synchronization signal is input at an unintended timing t3 as is the case with FIG. 9.

When misrecognition of the vertical synchronization signal occurs due to the disturbance in the middle of the read operation performed after selection of the unit pixel 230 in the pixel row <M> (timing t3), for example, the column counter value (not illustrated) is not yet counted up to the maximum value (n) so that resetting of the row counter value, the selection operation of a pixel row <0>, and the operation of reading an imaging signal from the unit pixel 230 in the pixel row <0> are performed without performing the de-selection operation of the unit pixel 230 in the pixel row <M>. As the de-selection operation of the unit pixel 230 in the pixel row <M> is not performed, the imaging signal read at this time is the overlap of the imaging signals from the unit pixels 230 in the pixel rows <M> and <0>.

Moreover, the normal synchronization signal is input at the predetermined cycle so that, even when the misrecognition of the synchronization signal occurs due to the disturbance, a normal synchronization signal (horizontal synchronization signal in this example) is input a predetermined time after the input of the previous synchronization signal (timing t4). The input of the normal synchronization signal is performed before completion of the read operation on the pixel row <0> that is initiated by the misrecognition of the synchronization signal caused by the disturbance, so that the counting up of the row counter value and the selection operation of a pixel row <1> are performed without performing the de-selection operation of the unit pixels 230 in the pixel row <M> selected at the time of the disturbance and the pixel row <0> selected when the normal synchronization signal is newly input (application of the drive signal φR <M> while VR is set to the level of Vfd_L as indicated with a dashed line immediately before the timing t4).

The de-selection operation is not performed on the pixel row <M> and the pixel row <0> that is selected when the normal synchronization signal is newly input, so that the imaging signal from then on is the overlap of the imaging signals from the pixel rows that are not de-selected (at least until the pixel rows not de-selected are selected again and de-selected after completing the read operation normally).

Therefore, when the vertical synchronization signal is input at a timing different from the normal timing in this variation, the overlap of imaging signals occurs at least among the frame being read, a next frame starting to be read by disturbance, and a next frame starting to be read by the synchronization signal that is input at the normal cycle, whereby the so-called frame drop occurs across the plurality of frames.

Figure 11:
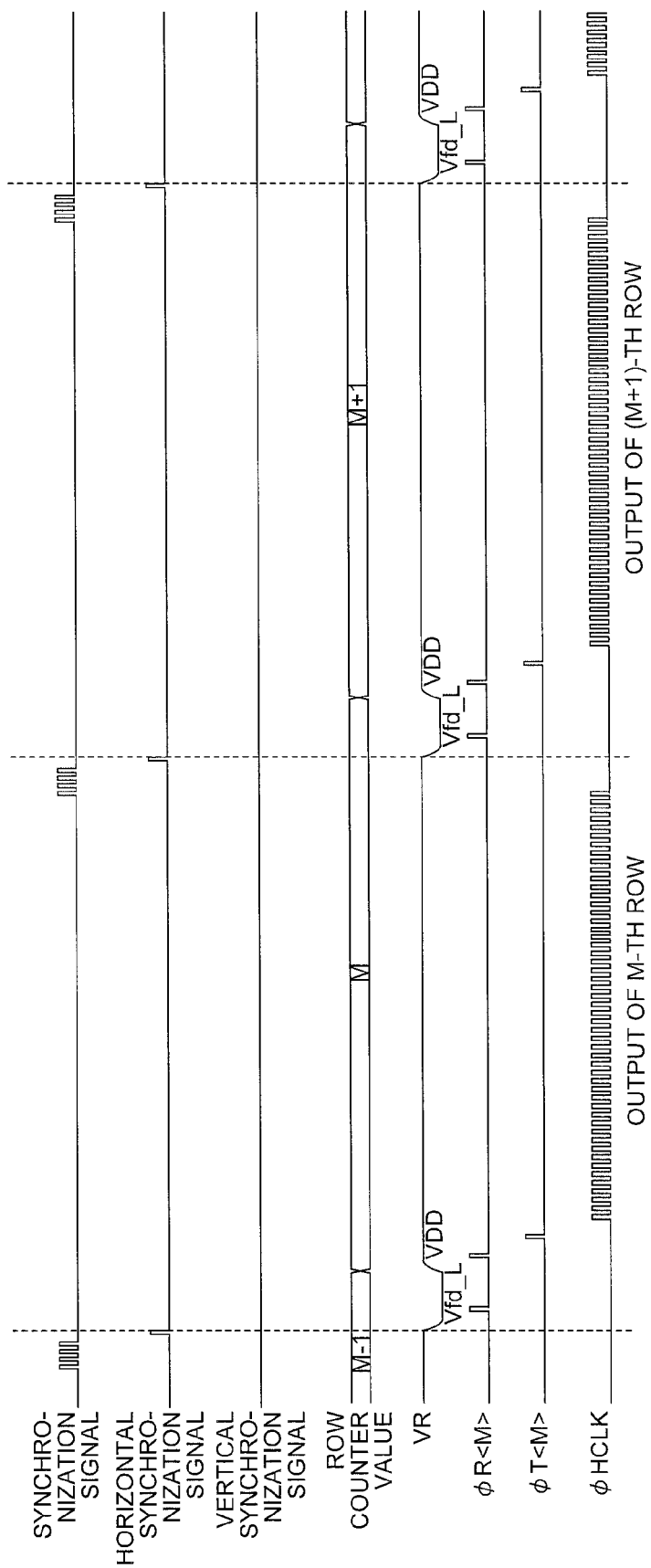
FIG. 11 is a timing chart illustrating a driving timing of an imaging device in normal time according to an embodiment of the present invention.

FIG. 11 is a timing chart illustrating a driving timing of an imaging device in normal time according to an embodiment of the present invention. The timing chart illustrates from the top a synchronization signal input from outside, a detected horizontal synchronization signal, a detected vertical synchronization signal, a row counter value, a variable voltage VR, a drive signal φR <M>, a drive signal φT <M>, and a drive signal φHCLK.

Upon input of a synchronization signal, a horizontal synchronization signal is detected so that the variable voltage VR is set to the level of Vfd_L (such as 1 V) at a timing corresponding to the fall of the horizontal synchronization signal.

Next, the pulsed drive signal φR <M> is applied to the gate of the pixel reset unit 236 in the pixel row <M−1> while the variable voltage VR is set to the level of Vfd_L, the pixel row being selected at the input of the synchronization signal. The de-selection voltage Vfd_L is thus applied to the gate of the pixel source follower transistor 237 in the pixel row <M−1>, thereby turning off the pixel source follower transistor 237. The selection of the unit pixel 230 included in the pixel row <M−1> is canceled in this manner (de-selection operation).

Next, the variable voltage VR is set to the level of VDD (such as 3.3 V). The row counter value is counted up from "M−1" to "M" at a timing corresponding to the rise of the variable voltage VR.

Next, the pulsed drive signal φR <M> is applied to the gate of the pixel reset unit 236 in the pixel row <M> while the variable voltage VR is set to the level of VDD. The power supply voltage VDD is thus applied to the gate of the pixel source follower transistor 237 in the pixel row <M>, thereby turning on the pixel source follower transistor 237. The unit pixel 230 included in the pixel row <M> is selected in this manner (selection operation).

At the same time, a variation distinctive of the unit pixel 230 to be read and a noise signal including noise generated in resetting a pixel are output from the unit pixel 230 to the vertical transfer line 239. The noise signal level is sampled to the sample capacitor 251 by switching the clamp switch 253 from on (high φVCL) to off (low φVCL).

After that, the pulsed drive signal φT <M> is applied to the gate of the transfer transistor 234 in the pixel row <M> while the variable voltage VR is set to the level of VDD. The charge that is photoelectrically converted by the photoelectric converter 231 is subjected to voltage conversion by the charge converter 233, so that a signal after subjected to the voltage conversion is read out to the vertical transfer line 239. The pixel output switch being omitted, the imaging signal (light-noise sum signal) subjected to the voltage conversion by the charge converter 233 is transferred to the vertical transfer line 239 through the pixel source follower transistor 237 and input to the noise removal unit 243. The noise removal unit 243 outputs an imaging signal (optical signal) by subtracting the noise signal sampled to the sample capacitor 251 from the imaging signal (light-noise sum signal).

Then, the horizontal scanning unit 245 successively applies a column selection pulse φHCLK <N> to a selected column <N> (N=0, 1, 2, . . . , n−1, n) of the light receiving unit 23 on the basis of the drive signal (φHCLK) supplied from the timing generation unit 25, transfers the imaging signal that is photoelectrically converted in each unit pixel 230 included in the pixel row <M> to the horizontal transfer line 258 through the noise removal unit 243, and outputs the signal to the output unit 31.

After that, the aforementioned processing is repeated when a next synchronization signal is input. In other words, upon input of the synchronization signal, the present embodiment in normal operation successively performs the de-selection operation of the pixel row selected at the time of the input, the counting up of the row counter value, the selection operation of the pixel row, and the operation of reading the imaging signal from the selected pixel row.

Note that when the vertical synchronization signal is input, the operation performed when the horizontal synchronization signal is input is performed for one to several cycles to thereafter reset the row counter value instead of counting it up.

When the horizontal or vertical synchronization signal is input from outside, namely when the column counter value is reset, the imaging device according to the embodiment of the present invention performs the de-selection operation of the selected pixel row on the basis of the horizontal or vertical synchronization signal and then counts up (increments) or resets the row counter value to perform the selection operation of a next pixel row.

Figure 12:
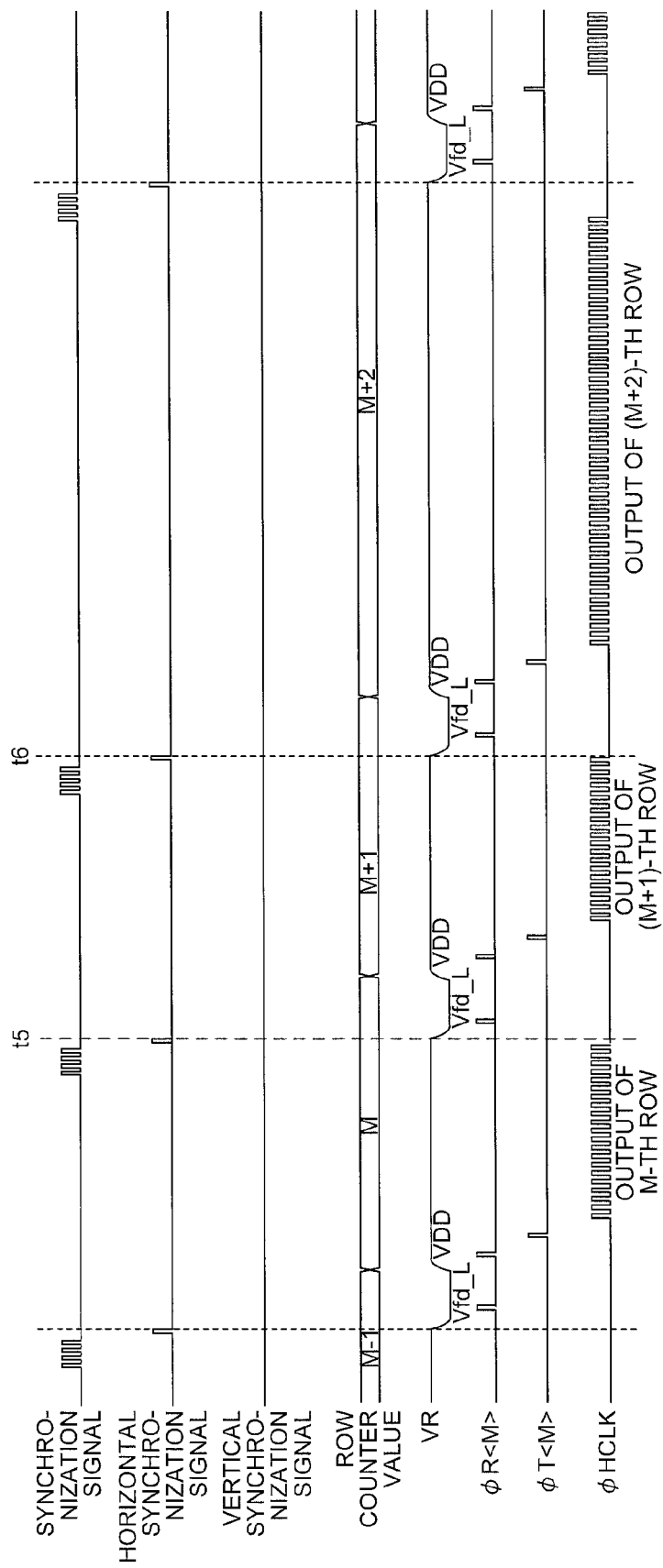
FIG. 12 is a timing chart illustrating a driving timing when a horizontal synchronization signal is input to the imaging device at a timing different from a normal timing, according to an embodiment of the present invention.

FIG. 12 is a timing chart illustrating a driving timing when a horizontal synchronization signal is input to the imaging device at a timing different from a normal timing, according to an embodiment of the present invention. Similar to FIG. 11, the timing chart illustrates from the top a synchronization signal input from outside, a detected horizontal synchronization signal, a detected vertical synchronization signal, a row counter value, a variable voltage VR, a drive signal φR <M>, a drive signal φT <M>, and a drive signal φHCLK.

While the synchronization signal is input at a predetermined cycle in normal operation, there is a case where the synchronization signal is erroneously input at an unintended timing different from the predetermined cycle due to disturbance caused by an electric knife or the like. FIG. 12 illustrates the operation when the synchronization signal is input at the unintended timing.

When misrecognition of the horizontal synchronization signal occurs due to disturbance in the middle of the read operation after selection of the unit pixel 230 in the pixel row <M> (timing t5), for example, the de-selection operation of the selected pixel row <M> is performed first in the present embodiment. After that, the counting up of the column counter value and the selection operation of the pixel row <M+1> are performed, followed by the initiation of the read operation of the imaging signal from the unit pixel 230 in the pixel row <M+1>. As the de-selection operation against the unit pixel 230 in the pixel row <M> is already performed, the imaging signal read at this time includes only the imaging signal from the unit pixel 230 in the pixel row <M+1>.

Moreover, the normal synchronization signal is input at the predetermined cycle so that, even when the misrecognition of the synchronization signal occurs due to the disturbance, a normal synchronization signal is input a predetermined time after the input of the previous synchronization signal (timing t6). The input of the normal synchronization signal is performed before completion of the read operation against the unit pixel 230 in the pixel row <M+1> that is initiated by the misrecognition of the synchronization signal caused by the disturbance. Upon input of the synchronization signal, as described above, the present embodiment is adapted to perform the de-selection operation against the selected pixel row <M+1> first, followed by the counting up of the row counter value, selection operation of a pixel row <M+2>, and read operation from the selected pixel row <M+2>. As a result, the de-selection operation is performed against the pixel row being read even when the synchronization signal is input while the imaging signal is being read, so that there is no overlap of imaging signals in a next pixel row.

Upon input of the horizontal synchronization signal from outside, as described above, the present embodiment is adapted to first perform the de-selection operation on the selected pixel row on the basis of the horizontal synchronization signal, followed by the counting up of the row counter value, selection operation of the pixel row, and read operation from the selected pixel row. The de-selection operation of the pixel row is thus performed normally even when the horizontal synchronization signal is input at a timing different from the normal timing, so that the overlap of the imaging signals does not occur. As a result, a fault such as the frame drop can be prevented with no influence of the imaging signal except the one from the pixel row being read.

Figure 13:
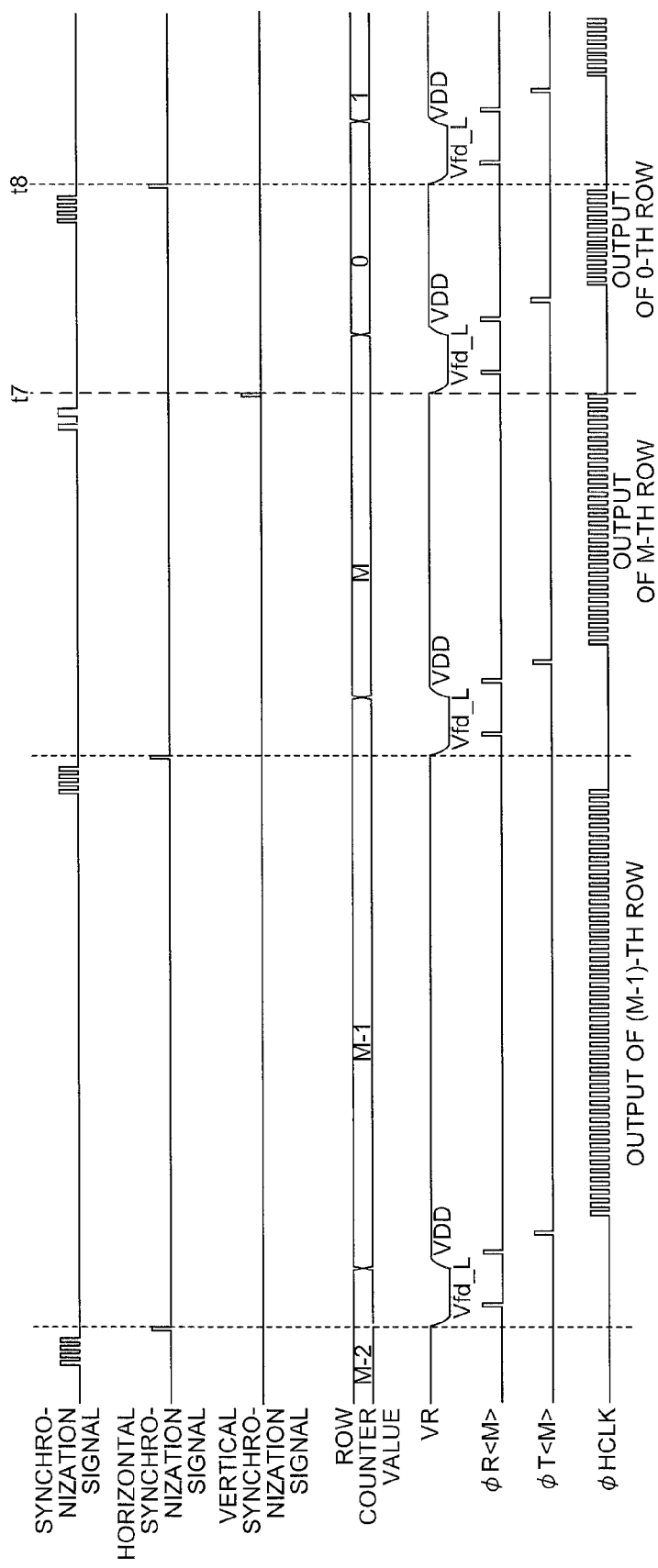
FIG. 13 is a timing chart illustrating a driving timing when a vertical synchronization signal is input to the imaging device at a timing different from a normal timing, according to an embodiment of the present invention.

FIG. 13 is a timing chart illustrating a driving timing when a vertical synchronization signal is input to the imaging device at a timing different from a normal timing, according to an embodiment of the present invention. Similar to FIGS. 11 and 12, the timing chart illustrates from the top a synchronization signal input from outside, a detected horizontal synchronization signal, a detected vertical synchronization signal, a row counter value, a variable voltage VR, a drive signal φR <M>, a drive signal φT <M>, and a drive signal φHCLK. FIG. 13 illustrates the operation when the synchronization signal is input at an unintended timing as is the case with FIG. 11.

When misrecognition of the vertical synchronization signal occurs due to disturbance in the middle of the read operation after selection of the unit pixel 230 in the pixel row <M> (timing t7), for example, the de-selection operation of the selected pixel row <M> is performed first in the present embodiment. After that, the resetting of the row counter value and the selection operation of the pixel row <0> are performed, followed by the initiation of the read operation of the imaging signal from the unit pixel 230 in the pixel row <0>. As the de-selection operation against the unit pixel 230 in the pixel row <M> is already performed, the imaging signal read at this time includes only the imaging signal from the unit pixel 230 in the pixel row <0>.

Moreover, the normal synchronization signal is input at the predetermined cycle so that, even when the misrecognition of the synchronization signal occurs due to the disturbance, a normal synchronization signal (horizontal synchronization signal in this example) is input a predetermined time after the input of the previous synchronization signal (timing t8). The input of the normal synchronization signal is performed before completion of the read operation on the pixel row <0> that is initiated by the misrecognition of the synchronization signal caused by the disturbance. Upon input of the synchronization signal, as described above, the present embodiment is adapted to perform the de-selection operation on the selected pixel row <0> first, followed by the counting up of the row counter value, selection operation of a pixel row <1>, and read operation from the selected pixel row <1>. As a result, there is no overlap of imaging signals in a next frame since the de-selection operation is performed on the pixel row being read, even when the counting up of the row counter value as well as the selection operation of the pixel row <1> are performed again upon input of the normal synchronization signal while performing the read operation from the selected pixel row.

Upon input of the vertical synchronization signal from outside, as described above, the present embodiment is adapted to first perform the de-selection operation on the selected pixel row on the basis of the vertical synchronization signal, followed by the resetting of the row counter value, selection operation of the pixel row <0>, and read operation from the selected pixel row. The de-selection operation on the pixel row is thus performed normally even when the vertical synchronization signal is input at a timing different from the normal timing, so that the overlap of the imaging signals does not occur. As a result, a fault such as the frame drop can be prevented with no influence of the imaging signal except the one from the pixel row being read.

According to the embodiments of the present invention, the update (counting up or resetting) of the row counter value is performed always after the de-selection operation of the selected pixel row on the basis of the synchronization signal input from outside, so that the overlap of the imaging signals can be avoided even when the synchronization signal is input at a cycle different from the normal cycle or misrecognized due to disturbance, and that the influence can be kept within the pixel row to which the synchronization signal is input (including the misrecognition caused by the disturbance). A fault such as the frame drop can be prevented as a result.

Moreover, according to the embodiments of the present invention, the overlap of the imaging signals can be avoided even when the synchronization signal is input at a cycle different from the normal cycle, so that a synchronization signal to reset the counter can be input at an arbitrary timing. The flexibility in designing the imaging device can be increased as a result.

Figure 14:
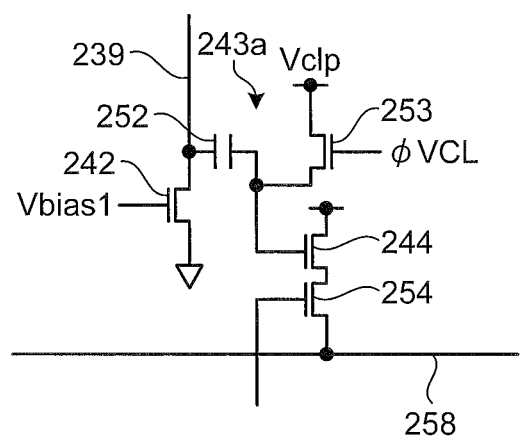
FIG. 14 is a schematic diagram illustrating another example of a noise removal unit according to an embodiment of the present invention.

While the noise removal unit 243 is configured by using the two capacitors, the sample capacitor 251 and the transfer capacitor 252, in the aforementioned embodiments, a noise removal unit 243a may instead be configured by using a transfer capacitor 252 alone as illustrated in FIG. 14. In this case, the noise removal unit 243a includes the transfer capacitor (AC coupling capacitor) 252 and a clamp switch (transistor) 253. A column source follower transistor 244 driven by a current source (not illustrated) connected to a horizontal transfer line 258 is further provided between the noise removal unit 243a and a column selection switch (second transfer unit) 254.

The transfer capacitor 252 is connected to a vertical transfer line 239 at one end side and the column source follower transistor 244 at another end side. One end side of the clamp switch 253 is connected to a signal line to which a clamp voltage Vclp is supplied. Another end side of the clamp switch 253 is connected between the transfer capacitor 252 and the column source follower transistor 244, while a drive signal φVCL from a timing generation unit 25 is input to a gate of the clamp switch. An imaging signal input to the noise removal unit 243a is a light-noise sum signal including a noise component.

The clamp switch 253 is turned on when the drive signal φVCL from the timing generation unit 25 is input to the gate of the clamp switch 253, whereby the transfer capacitor 252 is reset by the clamp voltage Vclp. The imaging signal, from which the noise is removed by the noise removal unit 243a on the basis of the Vclp voltage, is input to a gate of the column source follower transistor 244.

The column source follower transistor 244 is connected to a power supply voltage VDD at one end side and to one end side of a column selection switch 254 at another end side, while the imaging signal from which the noise is removed by the noise removal unit 243a is input to the gate of the column source follower transistor.

The noise removal unit 243a illustrated in FIG. 14 does not require a capacitor for sampling (sampling capacitor), so that the transfer capacitor 252 need only have the capacitance enough for the input capacitance of the column source follower transistor 244. In addition, the noise removal unit 243a occupies a smaller area on the first chip 21 due to the absence of the sampling capacitor.

The imaging element, the imaging device, the endoscope, the endoscope system and the method of driving the imaging element can prevent the frame drop caused by the synchronization signal input at the timing different from the timing at which the synchronization signal is to be input originally.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging sensor comprising:
 a plurality of pixels arranged into a two-dimensional matrix, configured to receive light from outside, and configured to generate and output an imaging signal according to an amount of light received;
 a first transfer line connected to the pixel and configured to transfer the imaging signal;
 a reference voltage generation circuit configured to generate a first voltage and a second voltage lower than the first voltage; and
 a control circuit configured to:
  perform a selection operation of selecting a selection target pixel from among the plurality of pixels in order to read the imaging signal out to the first transfer line and a de-selection operation of canceling the selection of the pixel being selected;
  perform the selection operation of selecting a new selection target pixel after performing the de-selection operation on the basis of a synchronization signal from outside; and
  update a counter value representing a pixel line in accordance with the synchronization signal,
 wherein the pixel includes:
  a photoelectric converter configured to perform photoelectric conversion according to the amount of light received and accumulate a charge;
  a first transfer transistor configured to transfer the accumulated charge;
  a charge converter configured to convert the transferred charge into the imaging signal;
  a pixel reset transistor connected to the reference voltage generation circuit and the charge converter and configured to reset the charge converter to the first voltage by supplying the first voltage generated by the reference voltage generation circuit; and
  a pixel amplification transistor including a gate connected to the charge converter, the pixel amplification transistor being connected to the reference voltage generation circuit and the first transfer line, being turned on at a time the first voltage is applied to the gate, and being turned off at a time the second voltage is applied to the gate, and wherein the control circuit is configured to perform the selection operation by turning on the pixel amplification transistor of the selection target pixel and perform the de-selection operation that cancels selection of the selected pixel by turning off the pixel amplification transistor of the selected pixel, and wherein the control circuit is configured to perform the selection operation of the pixel line represented by the updated counter value after performing the de-selection operation of the pixel line before the update every time the synchronization signal is input.

2. An endoscope comprising:

an elongated insertion structure configured to be inserted into a cavity; and the imaging sensor according to claim 1, wherein the imaging sensor is arranged at a distal end side of the elongated insertion structure.

3. A system comprising:

an elongated insertion structure configured to be inserted into a cavity; and the imaging sensor according to claim 1, wherein the imaging sensor is arranged at a distal end side of elongated insertion structure; and a processor configured to convert the imaging signal into an image signal.

4. A method of driving an imaging sensor including:

a plurality of pixels arranged into a two-dimensional matrix, configured to receive light from outside, and configured to generate and output an imaging signal according to an amount of light received, each pixel including:

a photoelectric converter configured to perform photo-electric conversion according to the amount of light received and accumulate a charge;

a first transfer transistor configured to transfer the accumulated charge;

a charge converter configured to convert the transferred charge into the imaging signal; a pixel reset transistor configured to reset the charge converter; and a pixel amplification transistor including a gate connected to the charge converter; and a first transfer line connected to the pixel and configured to transfer the imaging signal, the method comprising:

generating a first voltage and a second voltage lower than the first voltage;

resetting the charge converter to the first voltage by supplying the first voltage generated;

performing a de-selection operation which cancels, in a pixel line represented by a counter value, selection of a selected pixel in order to read the imaging signal out to the first transfer line on the basis of a synchronization signal from outside by turning off the pixel amplification transistor by applying the second voltage to the gate of the pixel amplification transistor;

updating the counter value representing the pixel line in accordance with the synchronization signal;

performing a selection operation which selects, in a pixel line represented by the counter value updated in the updating, a selection target pixel from among the plurality of pixels in order to read the imaging signal out to the first transfer line after the de-selection step by turning on the pixel amplification transistor by applying the first voltage to the gate of the pixel amplification transistor; and reading the imaging signal out to the first transfer line from the selected pixel.

* * * * *